United States Patent [19]

Carenzi et al.

[11] Patent Number: 4,766,137
[45] Date of Patent: Aug. 23, 1988

[54] 4-(ISOXAZOLYL)-THIAZOLE-2-OXAMIC ACIDS AND DERIVATIVES THEREOF

[75] Inventors: Angelo Carenzi, Busto Arsizio; Dario Chiarino, Monza; Davide Della Bella, Milan; Giancarlo Grancini, Nova Milanese, all of Italy

[73] Assignee: Zambon S.p.A., Vicenza, Italy

[21] Appl. No.: 845,694

[22] PCT Filed: Jul. 30, 1985

[86] PCT No.: PCT/EP85/00381
§ 371 Date: Mar. 13, 1986
§ 102(e) Date: Mar. 13, 1986

[87] PCT Pub. No.: WO86/00900
PCT Pub. Date: Feb. 13, 1986

[30] Foreign Application Priority Data
Jul. 31, 1984 [IT] Italy .................................. 22150 A/84

[51] Int. Cl.[4] .................. C07D 417/04; A61K 31/425

[52] U.S. Cl. .................................. 514/371; 548/195; 548/197

[58] Field of Search ................. 548/195, 197; 514/371

[56] References Cited

U.S. PATENT DOCUMENTS 4,246,271 1/1981 Cousse .............................. 548/195

*Primary Examiner*—Robert Gerstl
*Attorney, Agent, or Firm*—Stevens, Davis, Miller & Mosher

[57] ABSTRACT

4-(isoxazolyl)-thiazole-2-oxamic acids, esters and salts thereof; method for preparing them and intermediate compounds useful for their preparation.

Said compounds possess antiallergic and antianaphylactic activity and may be used in the pharmaceutical field.

Compositions for pharmaceutical use containing said compounds as the active ingredients are also described.

9 Claims, No Drawings

4-(ISOXAZOLYL)-THIAZOLE-2-OXAMIC ACIDS AND DERIVATIVES THEREOF

This invention relates to new compounds having antiallergic and antianaphylactic action and more particularly to derivatives of 4-(isoxazolyl)-thiazole-2-oxamic acids, their preparation and their use in the pharmaceutical field.

It is known that the disodium cromoglycate (Merck Index, IX ed., page 337) inhibits the release of mediators of allergic reactions provoked by antibody-antigen interactions.

Because of this property the disodium cromoglycate may be used in therapy as an antiallergic agent especially in asthamatic forms.

However, said compound is not absorbed orally and this drawback largely limits its field of applications.

To seek to overcome this drawback numerous other compounds were prepared which progressively modified the structure of the disodium cromoglycate until compounds structurally and chemically different from the parent compound were obtained.

Among these compounds may be mentioned the derivatives of phenyloxamic acid (J. Med. Chem., 21(9), 930, 1978) and 4-aryl-2-thiazole-oxamic acid (UK Patent Application No. 2,023,589—and European Patent Application No. 44442).

It has been now found that a valuable action is attained when the 4-position of a thiazole-2-oxamic acid is substituted by a 3 or a 5-isoxalyl group.

Therefor this invention relates to the compounds of formula:

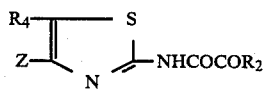
(I)

wherein Z is a group of formula

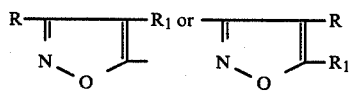

in which

R and $R_1$ which may be the same or different are a hydrogen or a halogen atom, a hydroxy group, a $C_{1-3}$ alkoxycarbonyl group, a $C_{1-3}$ alkyl group optionally substituted by hydroxy, $C_{1-3}$ alkoxy or alkoxy(1-3 C.)oxalyloxy, a $C_{1-3}$ alkoxy group optionally substituted by phenyl, or a phenyl group optionally substituted by halogen; and $R_2$ is a hydroxy group or $OR_3$ where $R_3$ is a $C_{3-6}$ cycloalkyl group or a $C_{1-3}$ alkyl group optionally substituted by phenyl or $C_{1-3}$ alkoxy; and $R_4$ is a hydrogen atom or a $C_{1-3}$ alkyl group; and when $R_2$ is a hydroxy group, their pharmaceutically acceptable salts with organic or inorganic bases.

Typical examples of R and $R_1$ include fluorine, chlorine, bromine, iodine, propoxycarbonyl, ethoxycarbonyl, methoxycarbonyl, methyl, ethyl, propyl, isopropyl, hydroxypropyl, hydroxyethyl, hydroxymethyl, propyloxypropyl, propyloxymethyl, methyloxyethyl, metoxymethyl, ethoxymethyl, ethoxalyloxypropyl (—$C_3H_6$ OCOCOOC$_2$H$_5$), propoxalyloxymethyl (—CH$_2$OCOCOOC$_3$H$_7$), ethoxalyloxymethyl (—CH$_2$OCOCOOC$_2$H$_5$), 2-bromophenyl, 2-iodophenyl, 2-chlorophenyl, 2,6-dichlorophenyl, 2-chloro-6-fluorophenyl, methoxy, ethoxy, propoxy, phenylethoxy and benzyloxy.

Preferred meanings of R and $R_1$ are hydrogen, bromine, chlorine, hydroxy, methyl, hydroxymethyl, methoxymethyl, ethoxalyloxymethyl, ethoxycarbonyl, phenyl, 2-chloro-6-fluorophenyl, benzyloxy and methoxy.

Typical examples of $R_3$ include cyclopropyl, cyclohexyl, methyl, ethyl, propyl, isopropyl, phenylmethyl, phenylethyl, phenylpropyl, methoxymethyl, propoxymethyl, ethoxyethyl, methoxyethyl and methoxypropyl.

Preferred meanings of $R_2$ are hydroxy and $OR_3$ wherein $R_3$ is ethoxyethyl, ethyl, cyclohexyl and phenylmethyl.

Typical examples of organic bases useful for preparing the salts according to this invention are the primary and secondary aliphatic amines optionally substituted by hydroxy and carboxy groups.

Specific examples of said organic bases are methylamine, isopropylamine, hexylamine, diethylamine, ethanolamine, 2-hydroxymethyl-2-amino-1,3-propanediol, glycine, alanine, valine, leucine, isoleucine, serine, threonine, aspartic acid, glutamic acid, arginine, lysine, cystine, cysteine, methionine, phenylalanine, tyrosine, tryptophan, histidine.

Depending on the meaning of the substituents, some of the compounds of formula I can exist in the form of isomers.

The isomers mixtures and the single isomers obtained by separation of the mixtures or by stereospecific synthesis are a further object of this invention.

The preparation of a compound of formula (I) comprises the reaction shown in the following Scheme 1

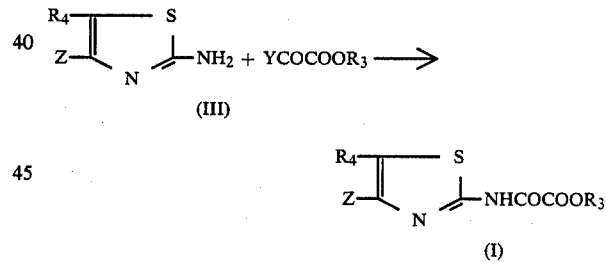
(I)

wherein Y is a halogen atom, and $R_4$, Z and $R_3$ have the above mentioned meanings, and, when desired, the hydrolization of the compound (I) and, optionally, the preparation of a pharmaceutically acceptable salt thereof with an inorganic or organic base.

In turn, the 2-amino-4-isoxazolyl-thiazole compound of formula (III) can be prepared by reacting a bromoacetyl-isoxazole compound of formula

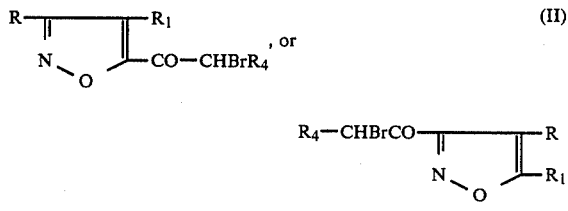

with thiourea.

This reaction is performed by heating the reaction mixture in a protic or aprotic polar solvent at a temperature preferably between 50° C. and 100° C.

The compound of formula (III) can be then reacted with a monoester oxalyl chloride to give the compounds of formula (I) wherein $R_2$ is an $OR_3$ group.

This reaction is performed preferably in pyridine or in an inert solvent in the presence of an acid-acceptor.

From the compounds of formula (I) wherein $R_2=OR_3$ are prepared by basic hydrolysis the free acids (I, $R_2=OH$).

The artisan will appreciate that the compounds of this invention may be prepared by alternative procedures with respect to those set forth above.

For example, the esters of formula (I) ($R_2=OR_3$) may also be prepared by transesterification of other esters of formula (I) or by reacting an acyl halide of an acid of formula (I) ($R_2=OH$) with a suitable alcohol of formula $R_3$—OH.

The compounds of formula (II) are in part compounds known as such or at the precursor level.

In any case, they are prepared by known techniques.

An example of synthesis is given in

Scheme 2

Reaction 1 of scheme 2 is performed by reacting the acyl chloride (IV) with diethylmalonate or a diethyl-2-alkylmalonate and carbon tetrachloride in the presence of magnesium, according to known techniques.

Reaction 2 of scheme 2 is performed by brominating the intermediate (V) with pyridine perbromide hydrobromide or other suitable brominating agents in a solvent such as carbon tetrachloride, chloroform, methyl chloride, etcetera.

Among the knonw compounds of formulas (V) and (II) may be mentioned
3-bromo-5-acetyl-isoxazole (European Patent No. 16,255),
3-methoxy-5-acetyl-isoxazole (Acta Chem. Scand., B, 28, 639, 1974),
3-bromo-5-bromoacetyl-isoxazole (European Patent No. 16,255),
3-methyl-5-acetylisoxazole (Gazz. Chim. It., 72, 242, 1942)
3-chloro-5-acetyl-isoxazole (Gazz. Chim. It., 91, 47, 1961) 5-hydroxymethyl-3-acetyl-isoxazole (Il Farmaco, ed. Sci. 39, 487, 1984)
3-bromoacetyl-5-phenyl-isoxazol (J. Med. Chem., 10, 411, 1967).

The compounds of formula (III) are new and are a further object of this invention.

The pharmacological evaluation showed that the compounds of this invention interfere with the appearance of the allergic pathology induced experimentally in the experimental animal. This interference proved to be marked and highly selective.

In the experimental animal, following treatment with the compounds of this invention with even large dosages, no important variations were recorded in the principal regulatory functions studied, such as for example the cardiocirculatory and the respiratory functions.

In addition, the coordination functions peculiar to the central nervous system activity were not influenced and no phenomena of a stimulating or sedative type appeared.

Neither in vitro nor in vivo was any direct antagonistic pharmacological action noted toward humoral or tissutal known mediators of the allergic pathology such as histamine, serotonin, bradykinin and SRS-A.

The pharmacological action of the compounds of this invention has been shown by a dual series of independent experiments in which was induced in the experimental animals (a) a passive cutaneous anaphylaxis experimental model; (b) an experimental model of systemic sensibilization approppriate for the appearance of bronchoconstriction by inhalation of the specific antigen.

The first test was performed in the rat in accordance with Goose J. and Blair A. M. J. N. (Immunology, 16, 749, (1969)) and Binaghi R. A. and Benacerraf B. (J. Immunol., 92, 920, (1964)); the production of hemocytotropic serum necessary for accomplishment of the test was obtained according to the method set forth by Mota I. (Immunology, 7, 681, (1964)).

The second test was accomplished on the guinea-pig, senzitized for 4–5 weeks by parenteral administration of ovalbumin as the allergen and adjuvant. The trigger reaction was induced following aerosol inhalation of the allergen until appearance of the characteristic signs of bronchoconstriction.

In these two tests the specific inhibitory activity of the compounds of this invention proved to be dose-dependent and clearly reproducible by the three selected administration ways: oral, peritoneal (ip) and venous (iv).

The Passive Cutaneous Anaphylaxis test in rat has given the following results:
2-ethoxyethyl 4-(3-methyl-5-isoxazolyl)-thiazole-2-oxamate, $ED_{50}=0.83$ mg/kg/os;
2-aminoethanol 4-(3-hydroxymethyl-5-isoxazolyl)-thiazole-2-oxamate, $ED_{50}=0.6$ mg/kg/os; 0.010 mg/kg/ip, 0.008 mg/kg/iv;
2-aminomethanol 4-(5-hydroxymethyl-3-isoxazolyl)-thiazole-2-oxamate, $ED_{50}=0.8$ mg/kg/iv;
2-ethoxyethyl 4-(5-hydroxymethyl-3-isoxazolyl)-thiazole-2-oxamate, $ED_{50}=1.8$ mg/kg/ip;
2-ethoxyethyl 4-(3-methoxymethyl-5-isoxazolyl)-thiazole-2-oxamate, $ED_{50}=0.98$ mg/kg/os;
2-ethoxyethyl 4-(3-carbethoxy-5-isoxazolyl)-thiazole-2-oxamate, $ED_{50}=0.08$ mg/kg/ip;
2-aminoethanol 4-(3-phenyl-5-isoazolyl)-thiazole-2-oxamate, $ED_{50}=1$ mg/kg/os, 0.1 mg/kg/ip, 0.06 mg/kg/iv;
2-ethoxyethyl 4-(3-phenyl-5-isoxazolyl)-thiazole-2-oxamate, $ED_{50}=0.8$ mg/kg/iv;
2-aminoethanol 4-(5-phenyl-3-isoxazolyl)-thiazole-2-oxamate $ED_{50}$, 2.3 mg/kg/os, 0.23 mg/kg/ip, 0.1 mg/kg/iv;

L-lysine 4-(5-phenyl-3-isoxazolyl)-thiazole-2-oxamate $ED_{50}=0.9$ mg/kg/os, 0.03 mg/kg/iv;

2-ethoxyethyl 4-(5-phenyl-3-isoxazolyl)-thiazole-2-oxamate, $ED_{50}=0.27$ mg/kg/ip, 0.15 mg/kg/iv;

2-aminoethanol 4-[3-(2-chloro-6-fluorophenyl)-5-isoxazolyl]thiazole-2-oxamate, $ED_{50}=0.015$ mg/kg/iv;

2-aminoethanol 4-(3-methoxy-5-isoxazolyl)-thiazole-2-oxamate, $ED_{50}=1.2$ mg/kg/ip; 0.5 mg/kg/iv;

2-ethoxyethyl 4-(3-hydroxy-5-isoxazolyl)-thiazole-2-oxamate, $ED_{50}=0.5$ mg/kg/ip.

In the same experiments, known reference compounds gave the following results:

4-phenyl-thiazole oxamic acid, $ED_{50}=2.8$ mg/kg/os; 3.5 mg/kg/ip, more than 1 mg/kg/iv;

4-(4-methoxyphenyl)-thiazole oxamic acid, $ED_{50}=2.9$ mg/kg/os;

2.6 mg/kg/ip; more than 1 mg/kg/iv;

4-(2-furyl)-thiazole oxamic acid, $ED_{50}=3.1$ mg/kg/os; 3.2 mg/kg/ip; more than 1 mg/kg/iv.

In addition to their high activity to oral route, a peculiar feature of the compounds of this invention is their very high activity by venous route. Those skilled in the pharmacological field will recognize that this means that the compounds of this invention possess a very high intrinsic activity, the lower activity by oral route being due to absorption problems. When a compound is endowed with a very high intrinsic activity a large opportunity to improve its oral activity is offered by routine selection of the most suitable derivatives thereof which overcome the absorption problem.

Both local and systemic tolerability appeared very favourable for all the compounds tested. No toxic phenomena were observed for doses greater than 0.5 g/kg via parenteral administration and 1.5 g/kg via oral route.

For all the compounds the ratio of pharmacological dose to tolerated dose proved to be quite favourable. The therapeutic dosage ranges from 5 to 500 mg/day.

The compounds of this invention are useful for treating the various pathological syndromes having a recognized allergic base, with localization either in the upper air tracts such as hay fever, bronchial asthma, or in the cutaneous tissues and superficial mucous membranes: hives, eczematose dermatitis, itching, allergic conjunctivitis.

Another object of the present invention are the pharmaceutical compositions containing as active ingredient the compounds of formula (I) or their pharmaceutically acceptable salts with organic or inorganic bases.

These compositions can contain the active ingredient together with pharmaceutically acceptable organic or inorganic solid or liquid excipients and can be suitable for topical, oral, parenteral, rectal or inhalatory administration.

The finished pharmaceutical forms can be solid, such as for example tablets, pills, capsules, powders, granules, suppositories; or liquid such as for example solutions, suspensions, emulsions, or semiliquids such as creams and ointments. They can even be prepared in such a manner that the release of the drug is prolonged after administration.

In addition to the excipients they can contain preservative, stabilizing, wetting and emulsifying agents, salts to regulate osmotic pressure, buffers, colourings, flavourings, etc.

They can be prepared according to known methods and can also contain other therapeutic ingredients.

In order to better illustrate the present invention the following examples are now given.

EXAMPLE A

1-[3-(2-chloro-6-fluorophenyl)-5-isoxazolyl]-ethanol 27.60 g (273 mmol) of triethylamine were added dropwise to a solution of 28.4 g (136.5 mmol) of alpha, 2-dichloro-6-fluorobenzaldoxime and 19.14 g (273 mmol) of 3-butin-2-ole in 250 ml of benzene kept under stirring at 8°–10° C.

When the addition was over the mixture was heated to 60° C.; after 1 hour the mixture was cooled and extracted with 10% hydrochloric acid and then with water.

Evaporation of the organic phase gave 31.1 of an oil which was purified by distillation and the fraction boiling at 140°–150° C. (0.3 mmHg) was collected.

1HNMR (CDCl$_3$): delta 7.6−7 (m, 3H); 6.4 (s, 1H); 5.1 (q, 1H); 1.6 (t, 3H).

EXAMPLE B (1) 3-(2-chloro-6-fluorophenyl)-5-acetylisoxazole

To a solution of 30 g (124 mmol) of 1-[3-(2-chloro-6-fluorophenyl)-5-isoxazolyl]-ethanol in 187 ml of acetic acid maintained under stirring at 5° C. were added dropwise 9.07 (90.7 mmol) of CrO$_3$ in 9.34 of water and 132 ml of acetic acid.

The mixture was kept overnight under stirring at room temperature; the solvent was then removed by evaporation and the residue was taken up with water, made neutral with sodium bicarbonate and extracted with ethyl ether.

The ethereal extracts were combined and washed with water, dried and evaporated to dryness; 27.8 g of an orange oily product were obtained. The oil was distilled under reduced pressure and the fraction boiling at 120°–122° C. (0.4 mmHg) was collected; yield, 23.7 g.

The oil was allowed to crystallize by standing and then recrystallized from isopropyl ether; m.p. 46°–47° C.

1HNMR (DMSO): delta 7.9–7.3 (m, 4H); 2.8 (s, 3H).

In a similar manner were obtained:

3-carbethoxy-5-acetylisoxazole

Yield, 82%; m.p. 67°–68° C. (isopropyl ether)

1HNMR (CDCl$_3$): delta 7.3 (s, 1H); 4.5 (q, 2H); 2.7 (s, 3H); 1.5 (t, 3H).

The starting compound, i.e. 1-(3-carbethoxy-5-isoxazolyl)-ethanol, was prepared according to European Pat. No. 28,355.

3-methoxymethyl-5-acetylisoxazole

Yield, 58.5%; colourless oil, b.p. 72°–74° C. (0.4 mmHg)

1HNMR (CDCl$_3$): delta 7.0 (s, 1H); 4.6 (s, 2H); 3.4 (s, 3H); 2.6 (s, 3H)

The starting compound, i.e. 1-(3-methoxymethyl-5-isoxazolyl)-ethanol, was prepared according to German Pat. No. 2,754,832.

(2) 3-benzyloxy-5-acetylisoxazole 2.2 g (90.5 mmol) of magnesium turnings were added under stirring to a solution of 14 g (87 mmol) of diethyl malonate in 78 ml of ethyl ether containing 63 g of anhydrous ethyl alcohol and 0.90 ml of carbon tetrachloride.

The mixture was refluxed for 2 hours and then was added dropwise a solution of 18.8 g (79 mmol) of 3-benzyloxy-5-isoxazolylcarbonyl chloride (Belgian Pat. No. 665,249) in 65 ml of ethyl ether.

The mixture was refluxed for 2 hours, cooled to room temperature and 159 ml of 2M sulfuric acid were added.

After vigorous stirring, the organic layer was separated, washed with water and evaporated to dryness.

The thus obtained oily residue (29.9 g) was added to a solution of 4.8 g of concentrate sulfuric acid in 36.3 ml of acetic acid and 25 ml of water; the mixture was refluxed for 8 hours.

The mixture was cooled to 20° C. and made neutral (pH 6.5) with 10M potassium hydroxide at constant temperature.

The mixture was extracted with chloroform; the combined organic extracts were evaporated to give an oily residue which was taken up with 150 ml of hexane. The crystalline precipitate was collected by filtration (6.7 g; Yield, 39%) and recrystallized from isopropyl ether. m.p. 77°–78° C.

1HNMR (CDCl$_3$): delta 7.5 (m, 5H); 7.2 (s, 1H); 5.4 (s, 2H); 2.5 (s, 3H).

EXAMPLE C (1) 3-chloro-5-bromoacetylisoxazole 28.65 g (179 mmol) of bromine in 20 ml of chloroform were added dropwise in 10 minutes to a solution of 25 g (172 mmol) of 3-chloro-5-acetylisoxazole containing 4.9 ml of glacial acetic acid while the reaction mixture was maintained under stirring at 48°–50° C.

After 5 minutes the mixture was poured into 330 g of water and crushed ice.

The organic layer was separated, washed with water, dried and evaporated to residual.

Yield, 37 g (96%) of an oily compound which can be purified by distillation; b.p. 97°–99° C. (2 mmHg).

1HNMR (CDCl$_3$): delta 7.00 (s, 1H), 4.37 (s, 2H).

In a similar manner were prepared the following compounds:

3-methoxy-5-bromoacetylisoxazole (from 3-methoxy-5-acetyl-isoxazole, Acta Chem. Scand. 28 B, 639, 1947);
Yield, 91%; deliquescent crystalline compound.
1HNMR (CDCl$_3$): delta 6.63 (s 1H); 4.33 (s, 2H); 4.00 (s, 3H).

3-benzyloxy-5-bromoacetylisoxazole
Yield, 83%; white crystalline compound, m.p. 80°–81° C. (isopropyl ether);
1HNMR (DMSO-d$_6$): delta 7.37 (s, 5H), 7,29 (s, 1H), 5.28 (s, 2H), 4.71 (s, 2H).

5-hydroxymethyl-3-bromoacetylisoxazole (from 5-hydroxylethyl-3-acetylisoxazole, Il Farmaco, Ed. sci, 39, 487, 1984); Yield 94%; oily compound, b.p. 160° C./0.3 mmHg,
1HNMR (CDCl$_3$): delta 6.72 (s, 1H), 4.85 (s, 2H), 4.60 (s, 2H).

3-methyl-5-bromoacetylisoxazole (from 3-methyl-5-acetylisoxazole, Gazz. Chim. Ital. 72, 242, 1942);
Yield, 87%; white crystalline compound, m.p. 44°–46° C. (isopropyl ether)
1HNMR (CDCl$_3$): delta 7.00 (s, 1H), 4.42 (s, 2H), 2.43 (s, 3H) 3-(2-chloro-6-fluorophenyl)-5-bromoacetylisoxazole
Yield, 85%; oily compound, b.p. 145°–150° C./0.3 mmHg
1HNMR (CDCl$_3$): delta 7.8–7 (m, 4H), 4.60 (s, 2H)

3-carbethoxy-5-bromoacetylisoxazole
Yield, 83%; white crystalline compound, m.p. 74°–75° C. (isopropyl ether)

1HNMR (CDCl$_3$): delta 7.5 (s, 1H), 4.52 (q, 2H), 4.50 (s, 2H), 1.5 (t, 3H)

3-methoxymethyl-5-bromoacetylisoxazole (from 3-methoxy-5-acetylisoxazole, Acta Chem. Scand. 28 B, 639, 1947); yield, 91%; oily compound.
1HNMR (CDCl$_3$): delta 7.1 (s, 1H), 4.4 (s, 2H), 3.4 (s, 3H). 1-(3-bromo-5-isossalolyl)-2-bromo-1-butanone
Yield, 98%; white crystalline compound, m.p. 53°–54° C. (hexane).
1HNMR (CDCl$_3$): delta 7.2 (s, 1H), 5.0 (t, 1H), 2.2 (m, 4H), 1.1 (t, 3H).

EXAMPLE D (1) 2-amino-4-(3-bromo-5-isoxazolyl)-thiazole

A mixture of 32.4 g (120.4 mol) of 5-bromoacetyl-3-bromoisoxazole and 18.4 g (240 mmol) of thiourea in 400 ml of anhydrous ethanol was refluxed for 90 minutes.

The solvent was removed by distillation and the residue was taken up while stirring with 750 ml of ethyl ether and 160 ml of 10% aqueous potassium hydroxide. The ethereal extract was separated and washed with 50 ml of ethyl ether.

The extracts and the ethereal washings were combined and washed with water till neutral, dried over sodium sulfate and then evaporated to dryness.

The crystalline residue (28.7 g; 97%) was purified by recrystallization from methanol, m.p. 160°–162° C.;
1HNMR (DMSO-d$_6$): delta 7.47 (s, 1H); 6.97 (s, 1H).

(2) 2-amino-4-(3-methoxy-5-isoxazolyl)-thiazole

A mixture of 9.2 g (41.8 mmol) of 3-methoxy-5-bromoacetylisoxazole and 6.36 g (83.6 mmol) of thiourea in 140 ml of methyl alcohol was refluxed for 90 minutes and then cooled for 1 hour with an ice bath.

The precipitate was collected by filtration and added to 120 ml of an 1% solution of sodium hydroxide while stirring vigorously.

The solution was allowed to stand for 30 minutes at room temperature, the precipitate was collected by filtration and washed with water till neutral.

Yield, 6.9 g (83.7%); after recrytallization from methyl alcohol the compound melts at 215°–217° C.
1HNMR (DMSO-d$_6$): delta 7.37 (s, 1H), 6.43 (s, 1H), 4.03 (s, 3H).

In a similar manner was prepared the 2-amino-4-(5-hydroxylmethyl-3-isoxazolyl)-thiazole,
Yield, 62.5%; m.p. 185°–187° C. (methyl alcohol)
1HNMR(DMSO-d$_6$): delta 7.3 (s, 1H), 6.7 (s,1H), 5.7 (t, 1H) 4.6 (d, 2H).

(3) 2-amino-4-(3-chloro-5-isoxazolyl)-thiazole

A mixture of 11.2 g (50 mmol) of 3-chloro-5-bromoacetylisoxazole and 7.6 g (100 mmol) of thiourea in 164 ml of ethyl alcohol was refluxed for 90 minutes and then cooled for 1 hour with an ice bath.

The precipitate was collected by filtration and added to a mixture of 25 ml of a 10% aqueous solution of sodium hydroxide and 100 ml of ethyl acetate under vigorous stirring.

The organic layer was separated, washed, dried and evaporated to dryness, Yield, 7.7 g (77%); after recrystallization from acetonitrile the compound melts at 169°–170° C.

1HNMR (DMSO-d$_6$): delta 7.4 (s, 1H), 6.9 (s, 1H).

In a similar manner the following compounds were prepared:

2-amino-4-(3-benzyloxy-5-isoxazolyl)-thiazole,
Yield, 76.5%; m.p. 129°–131° C. (acetonitrile)
1HNMR (CDCl$_3$): delta 7.3 (s, 1H), 6.5 (s, 1H), 5.4 (s, 2H).

2-amino-4-(5-phenyl-3-isoxazolyl)-thiazole, (from 5-phenyl-3-bromoacetylisoxazole, J. Med. Chem. 10, 411, 1967). Yield, 74.5%; m.p. 215°–216° C. (methyl alcohol).
Anal: S=12.98% (Calcd. 13.18%)

2-amino-4-(3-phenyl-5-isoxazolyl)-thiazole, (from 3-phenyl-5-bromoacetylisoxazole, J. Med. Chem. 10, 411, 1967). Yield, 65.5%; m.p. 192°–193° C. (acetonitrile).
Anal.: S=13.39% (Calcd. 13.18%)

2-amino-4-3-(2-chloro-6-fluorophenyl)-5-isoxazolyl-thiazole
Yield, 56.6%; m.p. 168°–169° C. (acetonitrile)
Anal: S=11.03% (Calcd. 10.84%)

2-amino-4-(3-methyl-5-isoxazolyl)-thiazole
Yield, 57%; m.p. 208°–210° C. (acetonitrile)
1HNMR (DMSO-d$_6$): delta 7.03 (s, 1H), 6.5 (s, 1H), 2.3 (s, 3H).

2-amino-4-(3-methoxymethyl-5-isoxazolyl)-thiazole
Yield, 49%; m.p. 137°–138° C. (acetonitrile)
1HNMR (DMSO-d$_6$): delta 7.3 (s, 1H), 6.6 (s, 1H), 4.5 (s, 2H), 3.4 (s, 3H).

2-amino-4-(3-bromo-5-isoxazolyl)-5-ethylthiazole
Yield, 70%; m.p. 151°–152° C. (acetonitrile)
1HNMR (DMSO-d$_6$): delta 6.8 (s, 1H), 3.0 (q, 2H), 1.2 (t, 3H).

(4) 2-amino-4-(3-hydroxymethyl-5-isoxazolyl)-thiazole 4.4 g (116.2 mmol) of sodium boron hydride were added portionwise to a solution of 13.9 (58.1 mmol) of 2-amino-4-(3-carbethoxy-5-isoxazolyl)-thiazole in 40 ml of dimethyl formamide and 80 ml of methyl alcohol under stirring at about 35° C.

When the addition was over, the reaction mixture was stirred at room temperature for 90 minutes and then was made acid by adding carefully 60 ml of 10% hydrochloric acid.

The reaction mixture was evaporated under reduced pressure, the residue was taken up with water and made alkaline with potassium carbonate.

The precipitate was collected by filtration and washed with water. Yield, 11.1 (97%); m.p. 184°–185° C. (acetonitrile).

1HNMR (DMSO-d$_6$): delta 7.4 (s, 1H), 6.6 (s, 1H), 4.6 (d, 2H).

(5) 2-amino-4-(3-carbethoxy-5-isoxazolyl)-thiazole

A solution of 54.8 (209 mmol) of 3-carbethoxy-5-bromoacetylisoxazole and 31.8 g (418 mmol) of thiourea in 685 ml of ethanol was refluxed for 90 minutes and then cooled for 1 hour with an ice bath.

The precipitate was collected by filtration and added to an aqueous solution of potassium bicarbonate under vigorous stirring.

The reaction mixture was shaken with ethyl acetate. The combined organic extracts were washed with water, dried and evaporated. Yield, 43.4 g (86.7%); m.p. 156°–157° C. (acetonitrile).

1HNMR (DMSO-d$_6$): delta 7.4 (s, 1H), 7.0 (s, 1H), 4.4 (d, 2H), 1.4 (t, 3H).

(6) 2-amino-4-(3-hydroxy-5-isoxazolyl)-thiazole hydrobromide A mixture of 13.5 g (68.5 mmol) of 2-amino-4-(3-methoxy-5-isoxazolyl)-2-thiazol and 135 ml of 48% hydrobromic acid was heated while stirring with an outer bath at 100° C. for one hour.

After cooling with a water/ice bath the precipitate was collected by filtration under reduced pressure and dried.

13.3 g (73.6%) of a white crystalline compound were obtained which were purified by crystallization from 1% hydrobromic acid.

1HNMR (DMSO-d$_6$): delta 7.5 (s, 1H); 6.6 (s, 1H).

EXAMPLE E (1) Ethyl 4-(3-bromo-5-isoxazolyl)-thiazole-2-oxamate

To a mixture of 7.38 g (30 mmol) of 4-(3-bromo-5-isoxazolyl)-2-thiazolamine and 3.50 g (34.6 mmol) of triethylamine in 60 ml of pyridine, stirred at a temperature not above 10° C. were added dropwise 4.71 g (34.5 mmol) of ethoxalyl chloride.

At the end of the addition the solution was stirred overnight and then diluted with 120 ml of water.

The precipitate was collected by filtration and washed on the filter with abundant water.

After vacuum drying at 50° C. the compound was recrystallized two times from 110 ml and 130 ml of acetonitrile respectively to give 6.90 g of a crystalline compound analitically pure; m.p. 196.5–197° C.

1HNMR (DMSO-d$_6$): delta 8.20 (s, 1H); 7.20 (s, 1H); 4.42 (q, 2H,); 1.40 (t, 3H).

In a similar manner was prepared the following compound: Ethyl-4-(3-phenyl-5-methyl-4-isoxazolyl)-thiazole-2-oxamate,
Yield, 78%; m.p. 157°–159° C. (acetonitrile)
1HNMR (DMSO-d$_6$): delta 7.6 (m, 5H), 7.3 (s, 1H), 3.2 (q, 2H), 2.6 (s, 3H), 1.3 (s, 3H).

(2) Ethyl 4-(3-methoxy-5-isoxazolyl)-thiazole-2-oxamate

To a mixture of 6.60 g (33.5 mmol) of 2-amino-4-(3-metoxy-5-isoxazolyl)-thiazole in 67 ml of pyridine while stirring at 5°–10° C. were added dropwise 5.25 g (38.5 mmol) of ethoxalyl chloride.

The reaction mixture was maintained under stirring overnight, then poured into 120 g of crushed ice and made acid with concentrate hydrochloric acid.

The mixture was extracted with 750 ml of 1,2-dichloroethane, the organic layer was separated and washed with water.

The organic extracts were evaporated; Yield, 9.40 g (94.5%); m.p. 204°–205° C.

1HNMR (DMSO-d$_6$): delta 8.10 (s, 1H), 6.6 (s, 1H), 4.4 (q, 2H), 4.0 (s, 3H), 1.4 (t, 3H).

In a similar manner were prepared the following compounds:
Ethyl 4-(5-phenyl-3-isoxazolyl)-thiazole-2-oxamate,
Yield, 47%; m.p. 169°–170° C. (ethyl alcohol)
1HNMR (DMSO-d$_6$): delta 8.2–7.4 (m, 5H), 8.1 (s, 1H), 7.5 (s, 1H), 4.4 (q, 2H), 1.4 (t, 3H).
Ethyl 4-(3-ethoxalyloxymethyl-5-isoxazolyl)-thiazole-2-oxamate,
Yield, 68%; m.p. 150°–151° C. (ethyl alcohol);
1HNMR (DMSO-d$_6$): delta 8.1 (s, 1H), 7.0 (s, 1H), 5.5 (s, 2H), 4.4 (q, 4H), 1.4 (t, 6H).
Benzyl 4-3-(2-chloro-6-fluorophenyl-5-isoxazolyl-thiazole-2-oxamate, Yield, 67%; m.p. 199°–200° C. (acetonitrile);
1HNMR (DMSO-d$_6$): delta 8.3 (s, 1H), 7.5 (m, 8H), 7.2 (s, 1H), 5.5 (s, 2H).

Cyclohexyl 4-3-(2-chloro-6-fluorophenyl-5-isoxazolyl-thiazole-2-oxamate,

Yield, 74%; m.p. 77°–78° C. (ethyl alcohol);
1HNMR (DMSO-d$_6$): delta 8.2 (s, 1H), 7.6 (m, 3H), 7.1 (s, 1H), 4.9 (m, 1H), 2.2–1.1 (m, 10H)

(3) 2-ethoxyethyl 4-(3-benzyloxy-5-isoxazolyl)-thiazole-2-oxamate

To a mixture of 5.6 g (20.5 mmol) of 2-amino-4-(3-benzyloxy-5-isoxazolyl)-thiazole in 37.4 ml of pyridine maintained under stirring at 5° C. were added dropwise 4.25 g (23.6 mmol) of 2-ethoxyethyloxalyl chloride.

The reaction mixture was maintained under stirring overnight, then poured into 100 g of crushed ice, made acid with concentrate hydrochloric acid and extracted with chloroform.

The chloroform extracts were washed with water, dried and evaporated to dryness. The residue (8.30 g) was recrystallized from 65 ml of acetonitrile; m.p. 142°–144° C.

1HNMR (DMSO-d$_6$): delta 8.2 (s, 1H), 7.6 (m, 5H), 6.7 (s, 1H), 4.5 (m, 2H), 3.8 (m, 2H), 3.6 (q, 2H), 1.2 (t, 3H).

In a similar manner were obtained the following compounds: 2-ethoxyethyl 4-(5-phenyl-3-isoxazolyl)-thiazole-2-oxamate, Yield, 82%; m.p. 146°–147° C. (acetonitrile)
1HNMR (DMSO-d$_6$): delta 8.1 (s, 1H), 8.1–7.5 (m, 5H), 7.5 (s, 1H), 4.5 (m, 2H), 3 (m, 2H), 3.6 (q, 2H), 1.2 (t, 3H).

2-ethoxyethyl 4-(3-phenyl-5-isoxazolyl)-thiazole-2-oxamate, Yield, 84%; m.p. 146°–147° C. (acetonitrile)
1HNMR (DMSO-d$_6$): delta 8.2 (s, 1H), 8.2–7.4 (m, 5H), 7.4 (s, 1H), 4.5 (m, 2H), 3.8 (m, 2H), 3.6 (q, 2H), 1.2 (t, 3H).

2-ethoxyethyl 4-3-(2-chloro-6-fluorophenyl)-5-isoxazolyl-thiazole-2-oxamate.

Yield, 87%; m.p. 140°–141° C. (acetonitrile)
1HNMR (DMSO-d$_6$): delta 8.2 (s, 1H), 7.7 (m, 3H), 7.2 (s, 1H), 4.5 (m, 2H), 3.8 (m, 2H), 3.6 (q, 2H), 1.2 (t, 3H).

2-ethoxyethyl 4-(3-methyl-5-isoxazolyl)-thiazole-2-oxamate,

Yield, 91%; m.p. 155°–156° C. (acetonitrile);
1HNMR (DMSO-d$_6$): delta 8.0 (s, 1H), 6.7 (s, 1H), 4.5 (m, 2H), 3.8 (m, 2H), 3.6 (q, 2H), 2.3 (s, 3H), 1.1 (t, 3H).

2-ethoxyethyl 4-(3-carbethoxy-5-isoxazolyl)-thiazole-2-oxamate,

Yield, 75%; m.p. 145°–146° C. (acetonitrile);
1HNMR (CDCl$_3$): delta 7.7 (s, 1H), 7.0 (s, 1H), 4.5 (q, 2H), 4.5 (m, 2H), 3.8 (m, 2H), 3.6 (q, 2H), 1.4 (t, 3H), 1.2 (t, 3H).

2-ethoxyethyl 4-(3-methoxymethyl-5-isoxazolyl)-thiazole-2-oxamate,

Yield, 86%; m.p. 136°–137° C. (ethyl alcohol)
1HNMR (DMSO-d$_6$): delta 8.1 (s, 1H), 6.8 (s, 1H), 4.6 (s, 2H), 4.4 (m, 2H), 3.7 (m, 2H), 3.6 (q, 2H), 3.4 (s, 3H), 1.2 (t, 3H).

2-ethoxyethyl 4-(5-hydroxymethyl-3-isoxazolyl)-thiazole-2-oxamate,

Yield, 58%; m.p. 159°–161° C. (acetonitrile);
1HNMR (DMSO-d$_6$): delta 8.0 (s, 1H), 6.9 (s, 1H), 4.7 (s, 2H), 4.5 (m, 2H), 3.8 (m, 2H), 3.6 (q, 2H), 1.2 (t, 3H).

2-ethoxyethyl 4-(3-hydroxy-5-isoxazolyl)-thiazole-2-oxamate, m.p. 217°–219° C. (acetonitrile);
1HNMR (DMSO-d$_6$); delta 8.00 (s, 1H), 6.37 (s, 1H), 4.43 (m, 2H), 3.73 (m, 2H), 3.53 (q, 2H), 1.13 (t, 3H).

2-ethoxyethyl 4-(3-bromo-5-isoxazolyl)-5-ethyl-thiazole-2-oxamate,

Yield, 92%; m.p. 128°–129° C. (acetonitrile);
1HNMR (DMSO-d$_6$): delta 7.0 (s, 1H), 4.4 (m, 2H), 3.7 (m, 2H), 3.5 (q, 2H), 3.1 (q, 2H), 1.3 (t, 3H), 1.1 (t, 3H).

ethoxyethyl 4-(3-bromo-5-isoxazolyl)-thiazole-2-oxamate

Yield, 70%; m.p. 162–164° C. (acetonitrile);
1HNMR (DMSO-d$_6$): delta 8.2 (s, 1H), 7.1 (s, 1H), 4.5 (m, 2H), 3.8 (m, 2H), 3.6 (q, 2H), 1.18 (t, 3H).

2-ethoxyethyl 4-(3-chloro-5-isoxazolyl)-thiazole-2-oxamate

Yield, 81%; m.p. 154°–156° C. (acetonitrile);
1HNMR (DMSO-d$_6$): delta 8.2 (s, 1H), 7.1 (s, 1H), 4.5 (m, 2H), 3.8 (m, 2H), 3.6 (q, 2H), 1.2 (t, 3H).

2-ethoxyethyl 4-(3-methoxy-5-isoxazolyl)-thiazole-2-oxamate

Yield, 78%; m.p. 142°–143° C. (acetonitrile);
1HNMR (DMSO-d$_6$): delta 8.10 (s, 1H), 6.58 (s, 1H), 4.5 (m, 2H), 4.02 (s, 3H), 3.8 (m, 2H), 3.60 (q, 2H), 1.18 (t, 3H).

(4) 2-methoxyethyl 4-(3-bromo-5-isoxazolyl)-thiazole-2-oxamate

To a mixture of 2.50 (10 mmol) of 2-amino-4-(bromo-5-isoxazolyl)-2-thiazole and 1.16 g (11.5 mmol) of triethylamine in 20 ml of pyridine stirred continously at a temperature of 5° C. were added dropwise 1.91 g (11.5 mmole) of 2-methoxy-ethyl-oxalyl chloride (prepared by adding 2-methoxy-ethanol to an excess of oxalyl chloride and collecting by distillation of the fraction with b.p. 124°–128° C./90 mmHg). At the end of the addition the solution was stirred for one night and then diluted with 50 ml of water.

The precipitate was collected by filtration under reduced pressure, washed abundantly on the filter with water, and dried under reduced pressure at 50° C., 3.10 g of raw material were obtained which were recrystallized twice from acetonitrile to give 2.30 (61%) of an analytically pure crystalline compound, m.p. 175.5°–177° C.;

1HNMR (DMSO-d$_6$): delta 8.17 (s, 1H); 7.13 (s, 1H); 4.50 (m, 2H,); 3.50 (m, 2H); 3.35 (s, 3H).

EXAMPLE F (1) 4-(3-bromo-5-isoxazolyl)-thiazole-2-oxamic acid

A suspension of 12.60 g (36.4 mmol) of ethyl 4-(3-bromo-5-isoxazolyl)-thiazole-2-oxamate in 500 ml of N/10 sodium hydroxide was stirred at 40° C. for 45 minutes.

The reaction mixture was cooled to room temperature, extracted twice with 150 ml of ethyl ether, treated with active charcoal, and filtered.

The filtrate was acidified with 60 ml of 1N hydrochloric acid and the precipitate was collected by filtration and washed on the filter abundantly with water.

Yield 9.80 g (84.5%); m.p. 217°–218.5° C. (dec.).
1HNMR (DMSO-d$_6$): delta 8.13 (s, 1H); 7.16 (s, 1H).

(2) 2-aminoethanol 4-(3-bromo-5-isoxazolyl)-thiazole-2-oxamate salt

A suspension of 2.85 g (8.95 mmol) of 4-(3-bromo-5-isoxazolyl)-thiazole-2-oxamic acid in 25 ml of ethanol was heated on a steam-bath while stirring. To this mixture were added 0.59 g (9.66 mmol) of ethanolamine in 10 ml of ethyl alcohol and 20 ml of water.

The solution was cooled to room temperature and then allowed to stand at 4° C. for one night.

The precipitate was collected by filtration, dried and recrystallized from 65 ml of a 2:1 ethyl alcohol/water mixture.

Yield, 2 g (59%); m.p. 190°–193° C. (dec.).

1HNMR (DMSO-$d_6$): delta 8.0 (s, 1H), 7 (s, 1H), 3.7 (m, 2H), 3.0 (m, 2H).

(3) tromethamine 4-(3-bromo-5-isoxazolyl)-thiazole-2-oxamate salt

To a solution of 3.20 g (26.4 mmol) of tromethamine in 75 ml of methanol, kept under stirring with slight refluxing, were added all at once 8.4 g (26.3 mmole) of 4-(3-bromo-5-isoxazolyl-2-thiazolyl oxamic acid.

The reaction mixture was cooled to room temperature and after approximately 15 minutes the precipitate was collected by filtration, washed on the filter with cold methanol, and dried.

The crude compound (7.10 g; 61.5%) was recrystallized from methanol; m.p. 183° C. (dec.);

1HNMR (DMSO-$d_6$+$D_2O$): delta 8.07 (s, 1H); 7.17 (s, 1H); 3.65 (s, 6H).

(4) L-lysine 4-(3-bromo-5-isoxazolyl)-thiazole-2-oxamate salt 2.6 (8.2 mmol) of 4-(3-bromo-5-isoxazolyl)-thiazole-2-oxamic acid were added to a solution of 1.25 (8.6 mmol) of L-lysine in 140 ml of 75% aqueous ethyl alcohol while refluxing and stirring.

After cooling to 0° C. the mixture was maintained under stirring for 3 hours. The precipitate was collected by filtration; yield, 2.7 (71%); m.p. 196°–197° C. (dec.)

1HNMR ($D_2O$): delta 7.5 (s, 1H), 6.5 (s, 1H), 3.9 (t, 3H), 3.1 (m, 2H), 2.2–1.3 (m, 6H).

In a similar manner were prepared the following compounds: 4-(3-methoxy-5-isoxazolyl)-thiazole-2-oxamic acid Yield, 82%; m.p. 224°–225° C. (dec.);

1HNMR (DMSO-$d_6$): delta 8.0 (s, 1H), 6.5 (s, 1H), 4.0 (s, 3H). 2-aminoethanol 4-(3-methoxy-5-isoxazolyl)-thiazole-2-oxamate salt, Yield, 83.7%; m.p. 214°–215° C. dec. (75% ethyl alcohol);

1HNMR (DMSO-$d_6$): delta 7.1 (s, 1H), 6.5 (s, 1H), 4.0 (s, 3H), 3.7 (m, 2H), 3.0 (m, 2H).

2-aminoethanol 4-(3-chloro-5-isoxazolyl)-thiazole-2-oxamate salt.

Yield, 71%; m.p. 211° C. dec. (70% ethyl alcohol);

1HNMR (TFAA): delta 8.1 (s, 1H), 7.1 (s, 1H), 3.7 (m, 2H), 3.0 (m, 2H).

2-aminoethanol 4-(5-phenyl-3-isoxazolyl)-thiazole-2-oxamate salt,

Yield, 68.5%; m.p. 210°–211° C. dec. (75% methyl alcohol);

1HNMR (DMSO $d_6$): delta 8.2–7.1 (m, 5H), 8.2 (s, 1H), 7.4 (s, 1H), 3.8 (m, 2H), 3.0 (m, 2H).

2-aminoethanol 4-(3-phenyl-5-isoxazolyl)-thiazole-2-oxamate salt,

Yield, 73%; m.p. 207°–208° C. dec. (85% ethyl alcohol);

1HNMR (DMSO-$d_6$): delta 9–7.3 (m, 6H), 7.4 (s, 1H), 3.8 (m, 2H), 3.1 (m, 2H).

L-lysine 4-(5-phenyl-3-isoxazolyl)-thiazole-2-oxamate salt,

Yield, 64.5%; m.p. 240°–241° C. dec. (20% methyl alcohol);

1HNMR (TFAA): delta 8.1–7.3 (m, 5H), 8.0 (s, 1H), 7.3 (s, 1H), 4.0 (t, 1H), 2.9 (m, 2H), 2.2–1.3 (m, 6H).

2-aminoethanol 4-(3-(2-chloro-6-fluorophenyl)-5-isoxazolyl-thiazole-2-oxamate salt, Yield, 56%; m.p. 230°–231° C., dec. (70% ethyl alcohol)

1HNMR (DMSO-$d_6$): delta 8.2–7.0 (m, 3H), 8.1 (s, 1H), 7.1 (s, 1H), 3.7 (m, 2H), 3.0 (m, 2H).

2-aminoethanol 4-(5-hydroxymethyl-3-isoxazolyl)-thiazole-2-oxamate,

Yield, 61%; m.p. 185°–187° C., dec. (methyl alcohol);

1HNMR (DMSO-$d_6$): delta 7.9 (s, 1H), 6.8 (s, 1H), 4.6 (s, 2H), 3.7 (m, 2H), 3.0 (m, 2H).

2-aminoethanol 4-(3-hydroxymethyl-5-isoxazolyl)-thiazole-2-oxamate,

Yield, 69%; m.p. 196°–197° C., dec. (75% methyl alcohol)

1HNMR (DMSO-$d_6$): delta 7.9 (s, 1H), 6.8 (s, 1H), 4.6 (s, 2H), 3.7 (m, 2H), 3.0 (m, 2H).

(5) Sodium 4-(3-methoxy-5-isoxazolyl)-thiazole-2-oxamate

A suspension of 11.9 (35 mmol) of ethoxyethyl 4-(3-metoxy-5-isoxazolyl)-thiazole-2-oxamate in 500 ml of N/10 sodium hydroxide was stirred at 40° C. for 30 minutes.

After cooling to 0° C., the precipitate was collected by filtration and dried.

Yield, 2.4 (23.5%); m.p. 320°, dec.

1HNMR (TFAA): delta 8.1 (s, 1H), 6.8 (s, 1H), 4.2 (s, 3H).

EXAMPLE G

(1) Granules containing 4-(3-bromo-5-isoxazolyl)-thiazole-2-oxamic acid (L)-lysine salt A mixture of 100 g of active ingredient, 155 g of lactose, 140 g of corn starch and 80 g of crystalline cellulose was stirred and the mixture was kneaded and granulated with a solution of 20 g of hydroxypropylcellulose in 400 ml of water and dried at 50° C. for 1 hour; then was passed through a 12 mesh screen to obtain granules which were dried at 50° C. for 10 hours.

(2) Suppository containing 4-(3-phenyl-5-isoxazolyl)thiazol-2-(2-ethoxyethyl)oxamate A mixture of 5–15 g of active ingredient and 180 g of Witepsol ® W-35 was heated and molten at 60° C. and the melt was cast into models so that the weight of each suppository was 1,5 g or 3 g. The cast melt was cooled and solidified to obtain suppositories.

(3) Tablets containing 4-(3-phenyl-5-isoxazolyl)-thiazole-2-oxamic ethanolamine salt A mixture of 100 g of active ingredient, 80 g of lactose, 70 g of corn starch and 40 g of crystalline cellulose was granulated in the conventional way.

The granulates was mixed with 4 g of magnesium stearate and formed into tablet each having a weight of 200 mg by a tabletting machine.

(4) Capsules containing
4-(3-methyl-5-isoxazolyl)-thiazole-2-(2-ethoxyethyl)ox-
amate A mixture of 100 g of active ingredient, 100 g of lactose, 60 g of corn starch 40 g of crystalline cellulose and 6 g of magnesium stearate was mixed and filled into hard capsules in an amount of 200 mg for capsule by using an encapsulating machine.

(5) Ampoules (injection solution) containing
4-(5-phenyl-3-isoxazolyl)thiazole-2-oxamic acid
(L)-lysine salt The active ingredient (100 parts by weight), 2 parts by weight of sodium pyrosulfite, 1 part by weight of disodium salt of ethylendiamine-tetraacetic acid, 17 parts by weight of sodium chloride are dissolved in a sufficient quantity of water and brought to 2000 parts by weight with the double distilled water. The solution was filtered and filled into 1 ml ampoules, finally the ampoules were sealed and sterilized. Each ampoule contains 50 mg of active ingredient.

(6) Inhalation Aereosol Preparation containing
4-(3-methyl-5-isoxazolyl)-thiazole-2-(2-ethoxyethyl)ox-
amate The active ingredient (1 to 20 parts), soya lecithin (0.20 to 4 parts) and mixture of propellant gases (Freon 11, 12 and 14) up to 100 parts was filled into aerosol containers with metering valve. The single dose can be adjusted in such a way that it provides 1 to 20 mg of active substance.

We claim:

1. A compound of formula

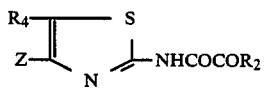

wherein Z is a group of formula

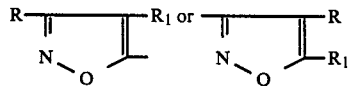

in which
R and $R_1$ which may be the same or different are a hydrogen or a halogen atom, a hydroxy group, a $C_{1-3}$ alkoxycarbonyl group, a $C_{1-3}$ alkyl group optionally substituted by hydroxy, $C_{1-3}$ alkoxy or alkoxy(1–3C)oxalyloxy, a $C_{1-3}$ alkoxy group optionally substituted by phenyl, or a phenyl group optionally substituted by halogen; and
$R_2$ is a hydroxy group or $OR_3$ where $R_3$ is a $C_{3-6}$ cycloalkyl group or a $C_{1-3}$ alkyl group optionally substituted by phenyl or $C_{1-3}$ alkoxy; and
$R_4$ is a hydrogen atom or a $C_{1-3}$ alkyl group;
and when $R_2$ is a hydroxy group, their pharmaceutically acceptable salts with organic or inorganic bases.

2. A compound according to claim 1, in which $R_3$ is an ethoxyethyl group.

3. A compound according to claim 1, in which $R_2$ is OH and pharmaceutically acceptable salts thereof with organic or inorganic bases.

4. A compound according to claim 1, in which Z is a

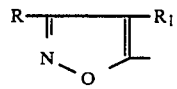

group, wherein
$R_1$ is hydrogen;
R is methyl, hydroxymethyl, methoxymethyl or phenyl; and
$R_2$ is a hydroxy group or $OR_3$ where $R_3$ is an ethoxyethyl group.

5. A compound according to claim 1, in which Z is a

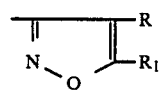

group, wherein
R is hydrogen,
$R_1$ is phenyl; and
$R_2$ is a hydroxy group.

6. A pharmaceutical composition having antiallergic and antianaphylactic activity containing an effective amount for the stated purpose of a compound according to any one of claims from 1 to 5, together with a pharmaceutically acceptable carrier.

7. A compound of formula

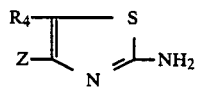
(III)

wherein Z is a group of formula

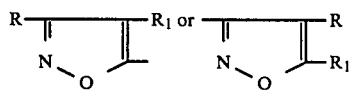

in which
R and $R_1$ which may be the same or different are a hydrogen or a halogen atom, a hydroxy group, a $C_{1-3}$ alkoxycarbonyl group, a $C_{1-3}$ alkyl group optionally substituted by hydroxy, $C_{1-3}$ alkoxy or alkoxy(1–3C)oxalyloxy, a $C_{1-3}$ alkoxy group optionally substituted by phenyl, or a phenyl group optionally substituted by halogen; and
$R_4$ is a hydrogen atom or a $C_{1-3}$ alkyl group.

8. A compound according to claim 7, in which $R_4$ is hydrogen and Z is a

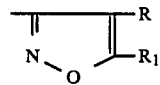

group, wherein
R is hydrogen; and
$R_1$ is phenyl.

9. A compound according to claim 7, in which $R_4$ is hydrogen, and Z is a

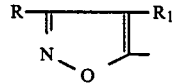

group, wherein
$R_1$ is hydrogen; and
R is methyl, hydroxymethyl, methoxymethyl or phenyl.

* * * * *